(12) United States Patent
Beyer et al.

(10) Patent No.: US 7,722,635 B2
(45) Date of Patent: *May 25, 2010

(54) BLOOD CLOT FILTER

(75) Inventors: Theodore Beyer, Queensbury, NY (US); Giorgio di Palma, Queensbury, NY (US); William A. Cartier, Hampton, NY (US)

(73) Assignee: AngioDynamics, Inc., Queensbury, NY (US)

( * ) Notice: Subject to any disclaimer, the term of this patent is extended or adjusted under 35 U.S.C. 154(b) by 532 days.

This patent is subject to a terminal disclaimer.

(21) Appl. No.: 10/991,013

(22) Filed: Nov. 16, 2004

(65) Prior Publication Data

US 2005/0288703 A1   Dec. 29, 2005

Related U.S. Application Data

(60) Provisional application No. 60/583,274, filed on Jun. 25, 2004, provisional application No. 60/614,757, filed on Sep. 29, 2004.

(51) Int. Cl.
  *A61M 29/00* (2006.01)
(52) U.S. Cl. .................................................. 606/200
(58) Field of Classification Search .................. 606/200

See application file for complete search history.

(56) References Cited

U.S. PATENT DOCUMENTS

| | | | | |
|---|---|---|---|---|
| 5,133,733 | A  * | 7/1992 | Rasmussen et al. | 606/200 |
| 5,344,427 | A  * | 9/1994 | Cottenceau et al. | 606/200 |
| 6,391,045 | B1 * | 5/2002 | Kim et al. | 606/200 |
| 6,506,205 | B2 * | 1/2003 | Goldberg et al. | 606/200 |
| 6,881,218 | B2 * | 4/2005 | Beyer et al. | 606/200 |

FOREIGN PATENT DOCUMENTS

FR         EP1258228 A1 *   5/2002

* cited by examiner

*Primary Examiner*—(Jackie) Tan-Uyen T Ho
*Assistant Examiner*—Melanie Tyson
(74) *Attorney, Agent, or Firm*—Harry K. Ahn; Abelman Frayne & Schwab (57) ABSTRACT

A compact blood clot filter having an alignment section that overlaps with a filter section in an axial direction is formed from a single tube without any welding points to provide high structural integrity, low profile and low manufacturing cost. The filter section has filter struts that extend radially and longitudinally from a hub. The alignment section has alignment struts in which the downstream end of each alignment strut forms a junction with the downstream end of an adjacent alignment strut while the upstream end of each alignment strut forms a junction with the upstream end of an adjacent alignment strut and with one of the filter struts to ensure symmetrical deployment of the filter struts and provide stable centering of the filter section.

11 Claims, 7 Drawing Sheets

BLOOD CLOT FILTER

CROSS REFERENCE TO RELATED APPLICATIONS

This application claims priority under 35 U.S.C. §119 (e) to U.S. provisional patent applications, Ser. No. 60/583,274, filed Jun. 25, 2004 and 60/614,757, filed Sep. 29, 2004, all of which are hereby incorporated by reference.

FIELD OF THE INVENTION

The present invention relates to a medical device and method for the capturing of thrombus. More particularly, the present invention relates to a permanent vena cava filter device for the capture of blood clots and method of manufacturing the same.

BACKGROUND OF THE INVENTION

Vena cava filters are used to capture potentially fatal pulmonary emboli at an anatomical location where they may pose less risk of pulmonary embolism for a patient. Since the vast majority of pulmonary emboli originate from the lower body, filters are mainly placed in the inferior vena cava (IVC).

Vena cava filters have been in use since the 1960s in a variety of configurations. Early filters required open surgical placement (Mobin—Uddin Filter; Kimray-Greenfield filter). Since the late 1970s, improvements in delivery were made and numerous filters were developed for minimally invasive percutaneous placement. These filters included the Greenfield filter, the Gianturco Bird's Nest Filter, the Vena Tech LGM filter, the Simon Nitinol filter and others.

Although addressing some desirable characteristics of a filter, the majority of the IVC filters presently on the market do not satisfy other desirable characteristics of an ideal filter. One of the attributes of an ideal vena cava filter is ease of deployment using minimally invasive percutaneous techniques as well as the ability of the device to provide optimal filtration while remaining centered within the vessel. Unfortunately, many filters are designed for ease of deployment but they either do not remain aligned within the vessel or have sub-optimal filtering capabilities.

An ideal device should capture blood clots while ensuring continued blood flow through the vessel. Blood flow disruption and turbulence often leads to thrombus formation and buildup at and around the filter. Studies have demonstrated that a conical filter configuration provides the optimal filtering efficiency. Filtering efficiency, for the purposes of this invention, can be defined as the capability of the device to capture and retain clots of a pre-determined size, the ability to maintain blood flow through the filter in the presence of captured clots, and the capability of dissolving or lysing the clots caught in the filter. Conical designs force clots toward the center of the filter, allowing blood flow passage around the clot. Continued flow of blood through the filter when a clot load is present ensures that captured clots are exposed to the lysing action of the blood flow.

Although conical filter configurations currently available on the market provide optimal filtering capabilities, these designs are prone to tilting and misalignment. When not in proper alignment, filtering ability is compromised. Misalignment can also lead to filter leg crossing, vessel perforation and migration of the device due to incomplete vessel wall engagement. Laminar blood flow is disturbed, effective lysing of captured clots decreases, and thrombus build-up occurs.

To address the misalignment problem, filtering cones have been designed with alignment mechanisms to prevent tilting. It is possible to build a simple centering cage base/conical filter combination design by attaching the base to the filter segment in series. This design, while exhibiting increased stability, is not practical due to the increased length of the device. The desired length of a typical IVC filter is between 3 and 5 centimeters. Longer lengths are undesirable because of the limited implantation space of the vena cava. For example, in some cases it is necessary to deploy a second filter due to malfunction of the initially placed filter. Shortening the filter segment may make the overall device length acceptable, but may result in sub-optimal filter strut angles. Alternatively, shortening the centering cage segment may compromise the alignment function of the device.

As with all permanent implant devices, the optimal device design maintains structural integrity of the device for the duration of implantation. Although rare, filters can develop fractures which have potentially fatal complications including filter migration into the right atrium and pulmonary embolism caused by compromised filtering efficiency. In addition to long term performance characteristics, it is desirable to provide an IVC filter that is simple and inexpensive to manufacture without requiring complicated assembly processes that might compromise the long-term integrity of the device or increase the overall cost of the device. IVC filter devices should also be sufficiently low profile to be delivered through a small diameter delivery system to minimize insertion site complications.

SUMMARY OF THE DISCLOSURE

A compact blood clot filter has an alignment section that at least partially overlaps with a filter section in an axial direction is provided. The filter section has filter struts that extend radially and longitudinally from a hub. The alignment section has alignment struts in which the downstream end of each alignment strut forms a junction with the downstream end of an adjacent alignment strut while the upstream end of each alignment strut forms a junction with the upstream end of an adjacent alignment strut and with one of the filter struts.

In one aspect of the invention, the upstream end of each alignment strut forms a junction with an upstream end of one of the filter struts.

In another aspect of the invention, the hub, filter struts and alignment struts are integral and formed from a single tubular element.

In another aspect of the invention, the alignment struts are arranged in a zigzag pattern.

In another aspect of the invention, the entire lengths of the alignment struts in a deployed state are positioned to rest against a vessel inner wall.

In another aspect of the invention, the downstream ends of the alignment struts extend radially away from its upstream ends and away from the longitudinal axis of the filter section toward the downstream direction such that the alignment struts are positioned at an angle relative to a vessel inner wall to minimize contact with the wall.

In yet another aspect of the invention, a compact blood clot filter having an alignment section that at least partially overlaps with a conical filter section in an axial direction is provided. The conical filter section has filter struts that extend radially and longitudinally from a hub. The alignment section has alignment struts in which the upstream end of each alignment strut forms a junction with the upstream end of an adjacent alignment strut and with one of the filter struts.

Various aspects of the present blood clot filter design provide high structural integrity, low manufacturing cost, symmetrical deployment of the filter struts, low profile and stable centering of the filter section.

BRIEF DESCRIPTION OF THE DRAWINGS

FIG. 3A and FIG. 3B are plan views of the vena cava filter device in an expanded state in which FIG. 3A shows a highlighted conical filter section and FIG. 3B shows a highlighted alignment/centering section.

DETAILED DESCRIPTION OF THE INVENTION

Figure 1:
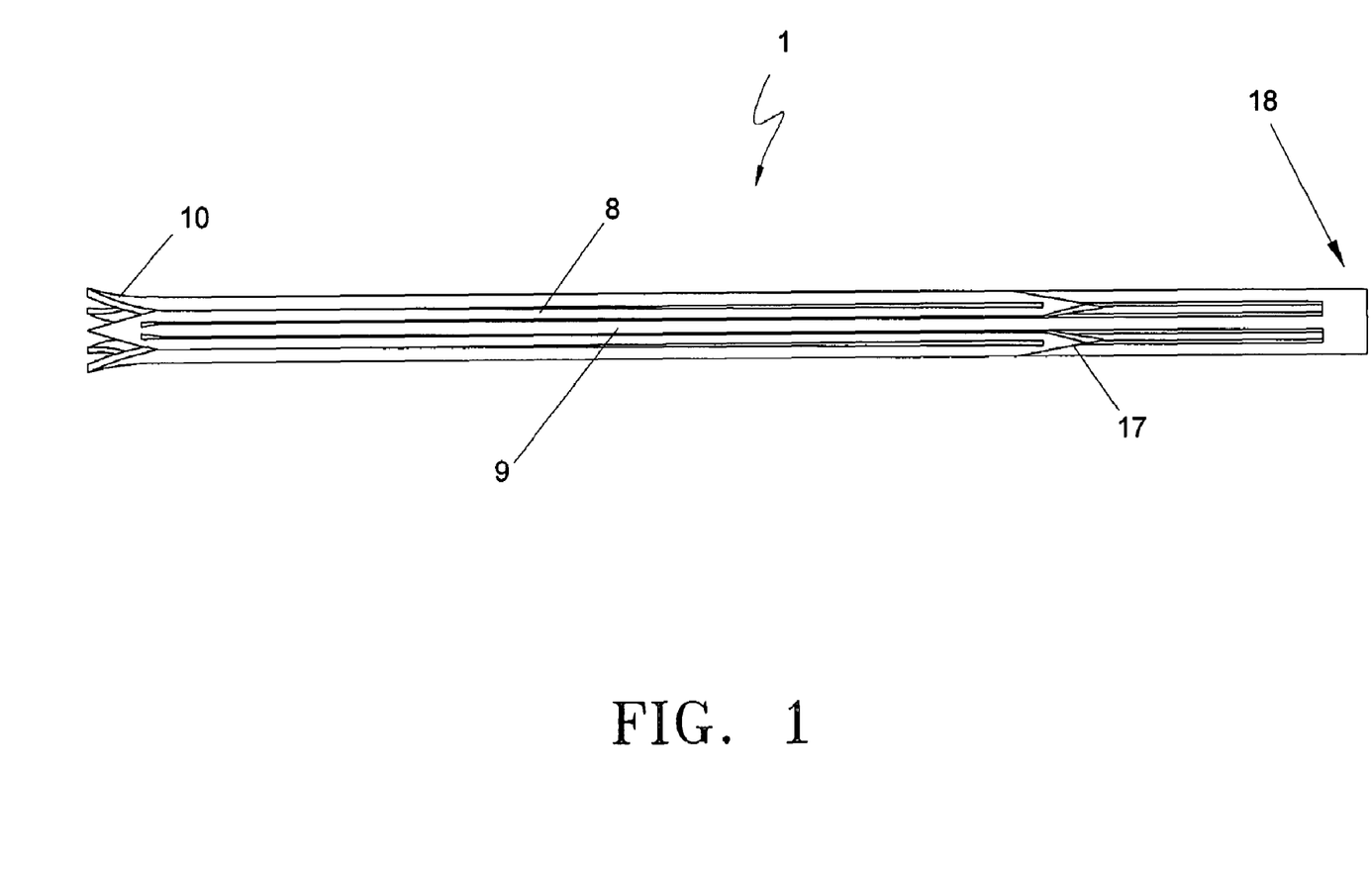
FIG. 1 is a plan view of the vena cava filter device of the current invention in a non-expanded state.

For purposes of the present application, the terms upstream and downstream refer to the direction of blood flow. Accordingly, blood flows from the upstream direction towards the downstream direction. Referring to FIG. 1, the vena cava filter of the present invention is shown from a plan view in a non-expanded undeployed state. The filter 1 includes a slender tubular construct 1 that can be percutaneously inserted through a catheter (not shown) into a patient. The tube is preferably of a material with shape-memory characteristics such as nitinol to allow self-expansion from the non-expanded collapsed state shown in FIG. 1. Nitinol is an alloy well suited for vena cava filters because of its superelastic characteristics, which enable it to return to a pre-determined expanded shape upon release from a constrained position. Other memory materials including stainless steel may be used.

Manufacturing the device involves cutting the tube into a desired configuration using laser-machining techniques commonly known in the art. Material is cut away from the tube in a pre-determined pattern to form the desired configuration. FIG. 1 illustrates the preferred pattern to which the tube is laser-cut to form the centering cage/section struts 8, filtering cone/section struts 9, upstream apexes/ends 10, and downstream apexes/ends 17. A hub 18 is an uncut section of the tube 1. After being laser cut, the tube 1 is annealed or heat-treated to form the expanded deployment shape, then constrained by a sheath or catheter (not shown) to the non-expanded profile as shown in FIG. 1. Other cutting techniques such as photoetching or acid etching may be used to achieve the desired pattern in the tube 1.

Advantageously, the tube manufacturing method according to the invention provides a unitary component that has no attachment points such as welding points. The singular tube construction avoids the necessity of welding or otherwise attaching individual wire elements together. The device is also easy to manufacture because of its tubular construction. As is well known in the art, welding or otherwise attaching shape-memory materials together is difficult, time-consuming and results in connection points that are more susceptible to long-term fatigue stress and loss of structural integrity than non-joined segments. By contrast, the lack of any welding points in the present invention (1) minimizes the possible complication of filter fracture caused from the loss of structural integrity of the filter wires over time; (2) simplifies assembly that results in decreased manufacturing costs, and (3) provides a lower unexpanded profile of the filter allowing use of smaller delivery systems.

Figure 2:
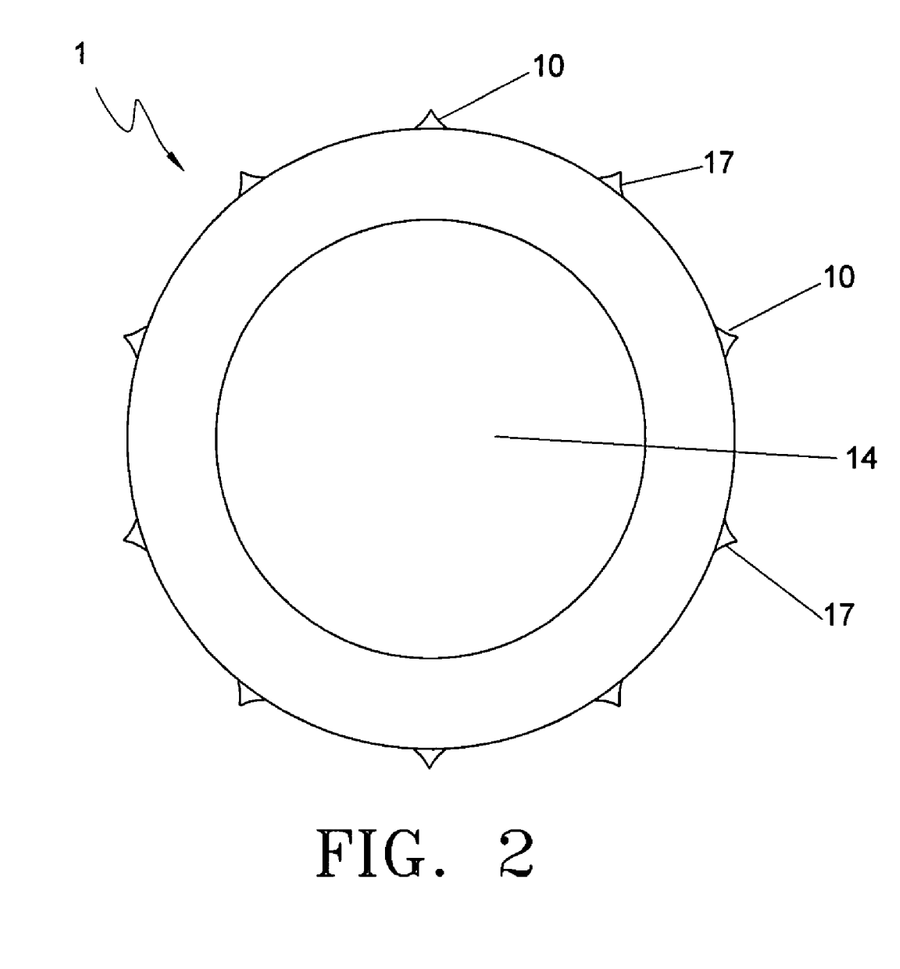
FIG. 2 is an end view of the vena cava filter device of FIG. 1.

FIG. 2 is an end view of the vena cava filter 1 depicted in FIG. 1 in a collapsed state. As shown, the outer diameter of the filter 1 is 0.071" for use with a small delivery sheath such as a 6 French size. The inner diameter of the filter 1 is approximately 0.051", providing a wall thickness of approximately 0.010". The inner wall of tube 1 defines a through channel 14 which is dimensioned to allow the passage of a 0.035" guidewire or other device (not shown) through the filter 1 to facilitate deployment in the vena cava.

Figure 3A:
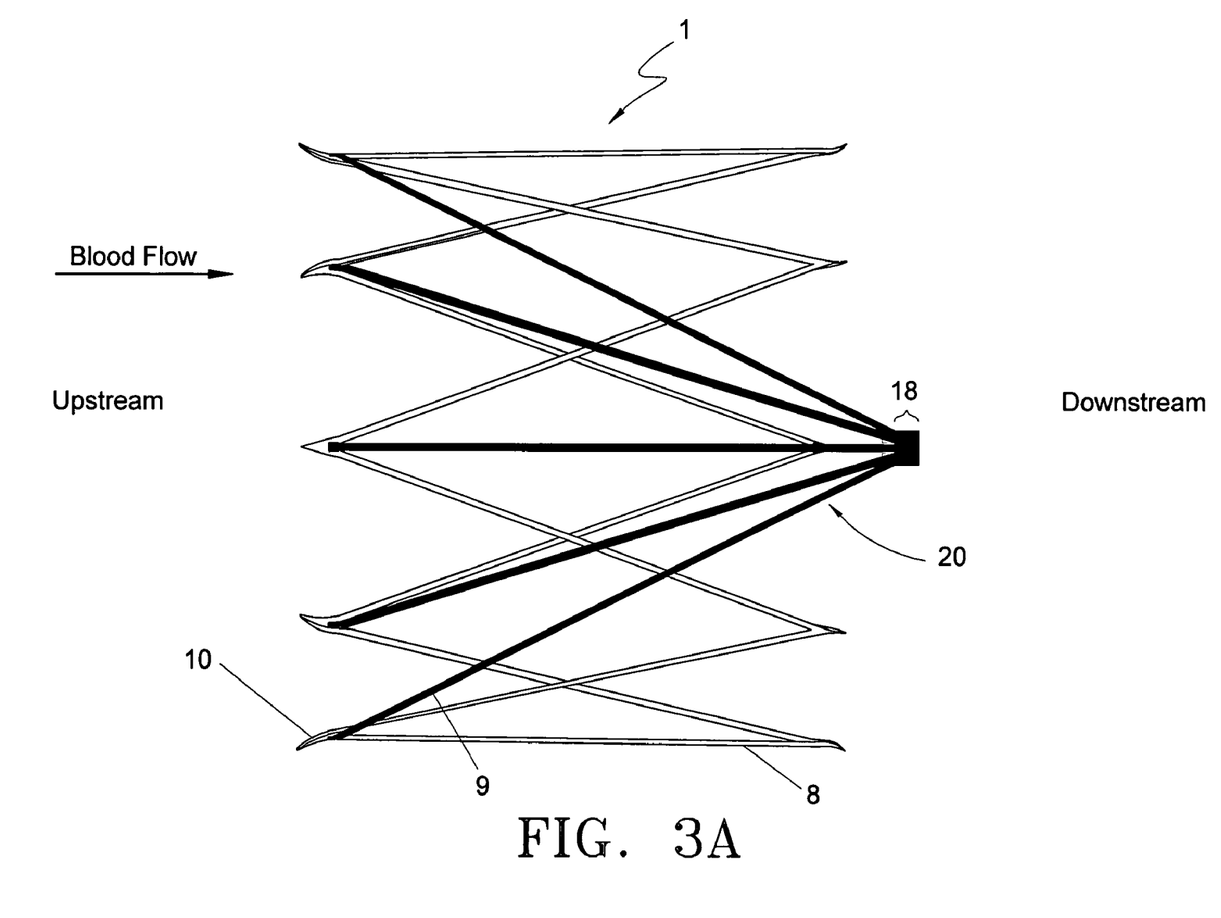
Figure 3B:
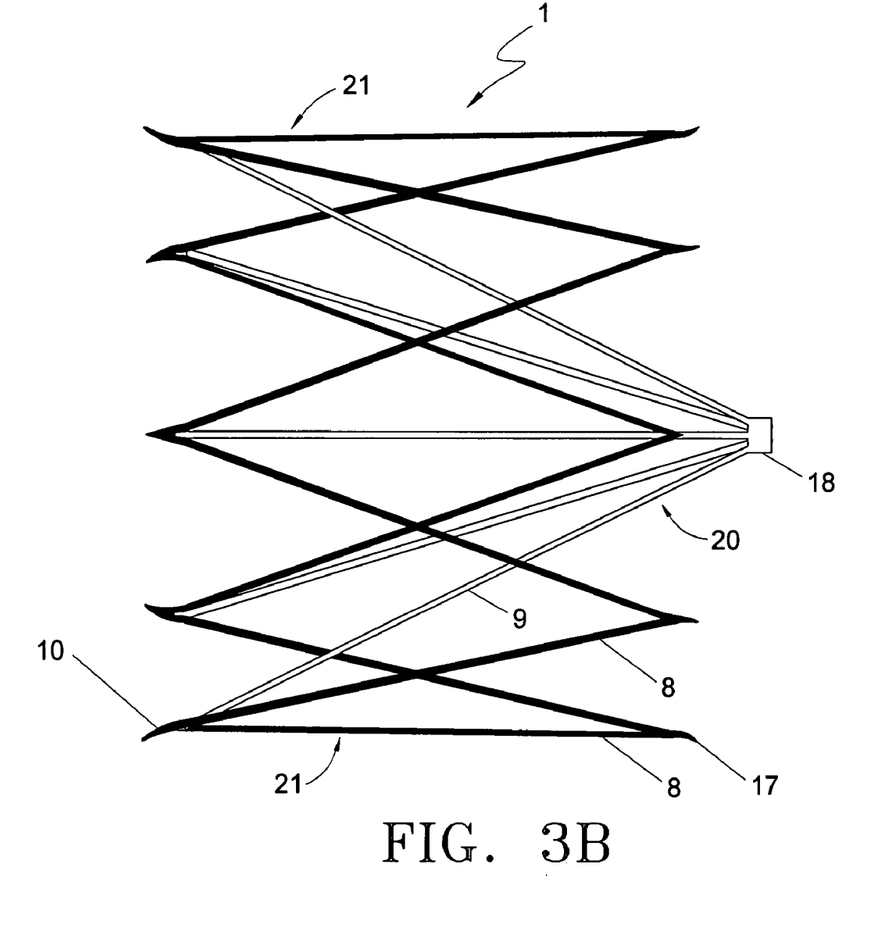

Referring now to FIG. 3A and FIG. 3B, plan views of the device 1 of the current invention is depicted in an expanded shape highlighting different functional components. FIG. 3A highlights the conical filter configuration/section 20 (bolded for clarity) of the filter 1. The conical filtering configuration 20 performs the clot capturing and lysing function by channeling thrombus to the center of the filter where it is trapped and lysed by surrounding blood flow. The conical filtering configuration 20 includes individual filtering struts 9 and a hub 18 which is a non-slotted section of the tube. Each filtering strut 9 extends axially and radially toward an upstream direction from the non-slotted section 18 of the tube to an upstream end/apex 10. Each upstream end 10 joins the upstream end of one filtering strut 9 and the upstream ends of two adjacent alignment struts 8. As shown, there are five filtering struts, although other configurations are possible.

FIG. 3B highlights the centering or alignment section/cage 21 (bolded for clarity) of the filter 1. Although highlighted separately in FIG. 3A and FIG. 3B for clarity purposes, the centering section 21 and conical filter section 20 are formed of a single tube with no welded connection points, thereby providing an integral filtering and alignment sections. The centering section 21 is adapted for placement against the vena cava wall, and acts to provide central alignment of the conical filter section 20 within the vessel. The centering section 21 is formed of a series of alignment struts (centering cage struts) 8. As shown, there are ten alignment struts, although other configurations are possible.

Each alignment strut 8 has an upstream end/apex 10 and a downstream end/apex 17. In the embodiment shown, each alignment strut 8 contacts with the vessel wall for the entire length of the strut, from the upstream end 10 to the downstream end 17. The downstream end 17 of each alignment strut 8 forms a junction with the downstream end of an adjacent alignment strut. At the upstream end of the filter 1, the upstream end 10 of each alignment strut 8 forms a junction with an upstream end of an adjacent alignment strut 8 and an upstream end of one of the filter struts 9. The series of alignment struts 8 together forms a single zigzag stent-like configuration 21 that lies against the inner vessel wall.

The interconnecting arrangement of the alignment struts 8 to each other ensures that each strut is symmetrically deployed around the inner vessel wall. Leg crossing or entanglement during or after deployment is avoid by the interconnecting design of the alignment struts 8, which ensures that equal spacing is maintained between each apex at both the upstream and downstream ends of the filter. The symmetrical deployment, anchoring and alignment features of this design allow the filter to be consistently placed in vena cavas of varying dimensions and shapes.

Each alignment strut 8 may include integral barbs (pointed ends) at the upstream end 10 and downstream end 17. The barbs may be formed by angling the ends of alignment strut 8 outwardly so as to cause it to embed in the vessel wall when deployed (see FIG. 5). In one embodiment, the barbs are formed by the laser-cutting process and subsequent annealing to form the final barb curve. Because the barbs are formed directly from the tubular construct 1, welding or otherwise attaching the barbs to the filter is eliminated. Not only does this design reduce manufacturing costs and time, but it also increases the overall structural integrity of the filter 1.

The barb at each downstream end 17 is oriented so as to stabilize the filter 1 and prevent migration in a downstream direction, that is, towards the heart if the filter 1 is placed in the inferior vena cava. As the clot load on the filter increases, the barbs at the downstream end 17 are driven further inward into the vessel wall to provide enhanced fixation. The longitudinal contact of the alignment struts 8 against the vessel wall prevents the downstream end 17 from completely perforating the vessel wall as well as enhance fixation by increased filter-wall contact The barbs at the upstream end 10 of the filter are angled outwardly toward the upstream direction and also embed in the vessel wall when deployed. The barb formed from the upstream end 10 is oriented so as to stabilize the filter 1 and prevent migration in the upstream direction. This fixation arrangement prevents migration during retrograde flow and normal body movements. Again, the longitudinal contact of the alignment struts 8 against vessel wall prevents the upstream ends 10 from completely perforating the vessel wall and causing vein trauma. Other barb configurations are also possible, including barbs of differing profiles and locations along the alignment struts.

The stent-like centering section 21 thus provides a structure that ensures that the conical filtering section 20 remains centered within the vena cava lumen. The alignment struts 8 also provide increased longitudinal contact with the vessel wall, which decreases the chance of filter migration after implantation. Barbs 10, 17 positioned at the upstream and downstream ends of the filter also prevent longitudinal movement of the filter in either upstream or downstream direction. The interconnected nature of all struts ensures that the vessel wall contact is symmetrical with respect to the longitudinal axis of the filter, providing for optimal centering of the filter section 20. Independent separate movement of the centering struts 8 from the filter section 20 is eliminated by the interconnected design. Thus, advantageously, problems of misalignment and leg crossing found in prior art designs in which the centering mechanism does not include interconnecting alignment structures are eliminated with the present invention.

Figure 4:
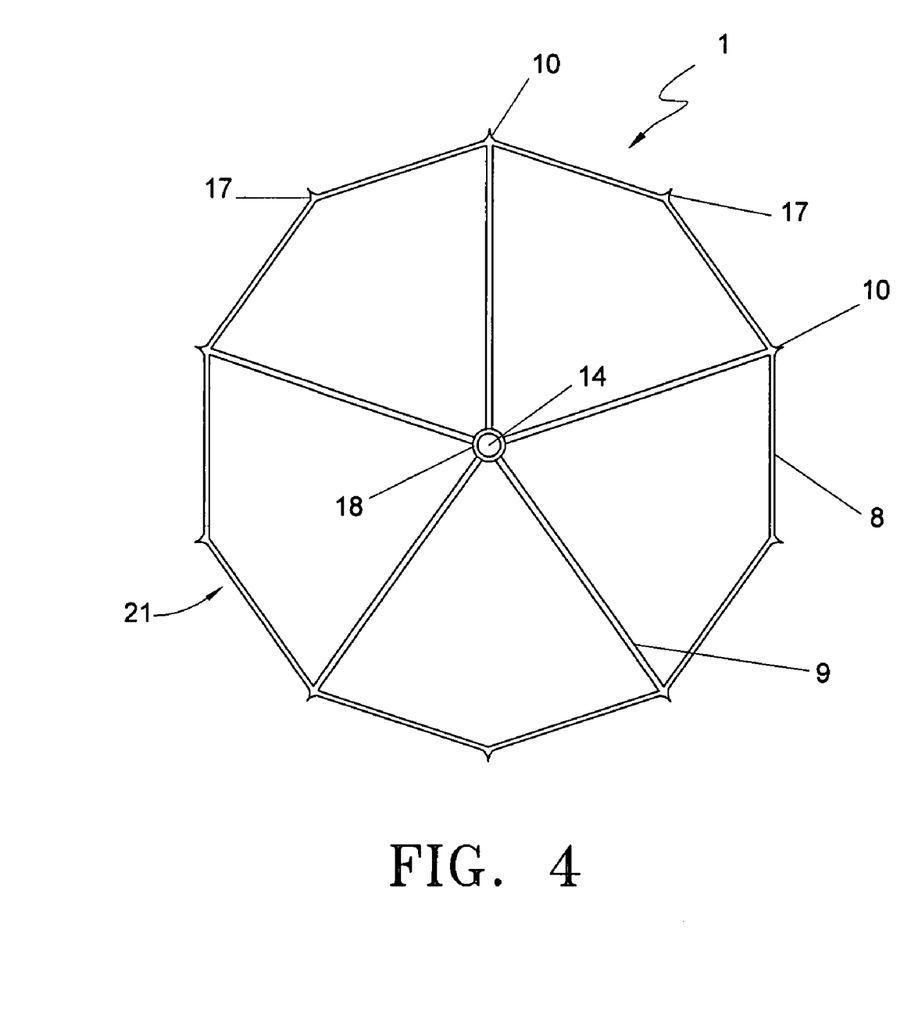
FIG. 4 is an end view of an expanded vena cava filter of the present invention.

Referring now to FIG. 4, an end view of the filter device 1 in an expanded/deployed state is shown. The alignment struts 8 combine to provide the centering section 21, which rests against the vessel wall. Barbs at apexes 17 provide primary fixation against downstream migration. The filter legs 9 extend outward from the non-slotted section 18 to intersect with the alignment struts 8 at the upstream apexes 10, which provide a secondary fixation function. The filtering struts 9 provide the clot capturing and filtering function. The through channel/hole 14 provides a lumen through which a guidewire or other medical device accessories can be advanced to assist in placement of the filter 1. The alignment struts 8 assure that the filtering struts 9 remain symmetrically positioned within the vessel.

Thus, the stabilizing alignment section 21, which is configured in a zigzag pattern, ensures that the centering alignment of the conical filter section 20 is maintained throughout the implantation period of the device. This unique design overcomes prior art problems with cone misalignment and tilting and the resulting complications of blood flow turbulence, compromised lysing capability and thrombus buildup.

Figure 5:
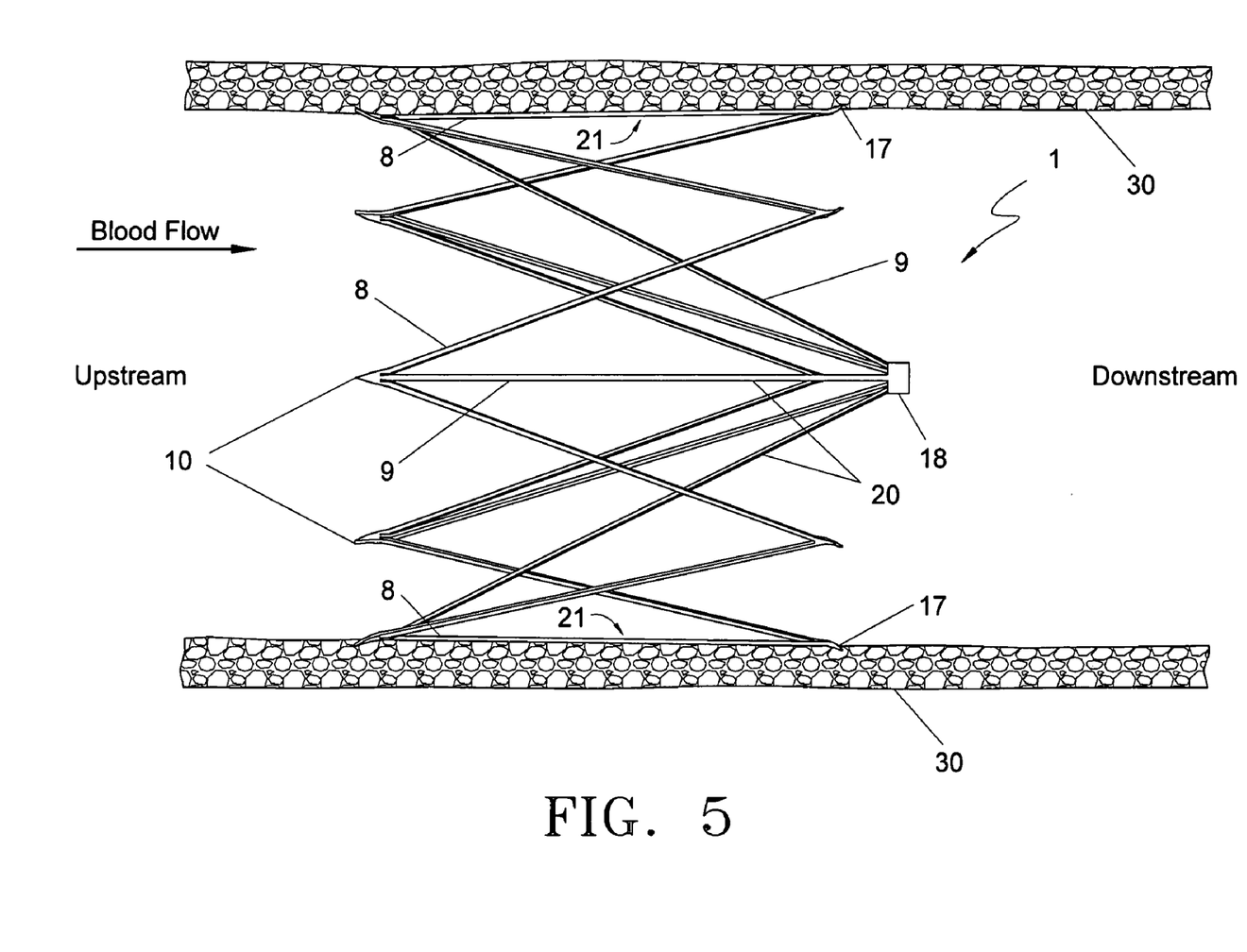
FIG. 5 is a plan view of the vena cava filter deployed within a vessel.

Referring to FIG. 5, the vena cava filter 1 is depicted in a deployed position within the vessel 30. The overlapping configuration of the conical filter section 20 and the alignment section 21 in the longitudinal axial direction represents another novel aspect of the current invention. The stabilizing alignment section 21 with the filter section extending from the upstream ends 10 provides a device with a filter segment length for optimal conical filter angle relative to the vessel wall. This overlapping design minimizes the overall length of the device when deployed and also provides a mechanism for accurate, reliable and easy placement during deployment.

The overall short length of the device provides flexibility in placement locations. For example, placement of the filter to prevent pulmonary embolism originating from the upper extremities requires a smaller length filter because of the anatomy of this vein. The available space to place the filter in the superior vena cava is limited by the right atrial junction and the intersection of the left and right brachiocephalic veins. The overlapping, coaxial design of the present filter 1 allows for deployment in limited length vein segments such as the superior vena cava without compromising other clinical requirements such as filtering efficiency and self-centering. Thus, the filter 1 provides a centering section 21 of sufficient length for self-centering and a conical filter section 20 with sufficient length for optimal cone angle without significantly increasing the length of the device. The filter design provides for reliable and symmetrical deployment without complicated deployment systems and/or steps.

Figure 6:
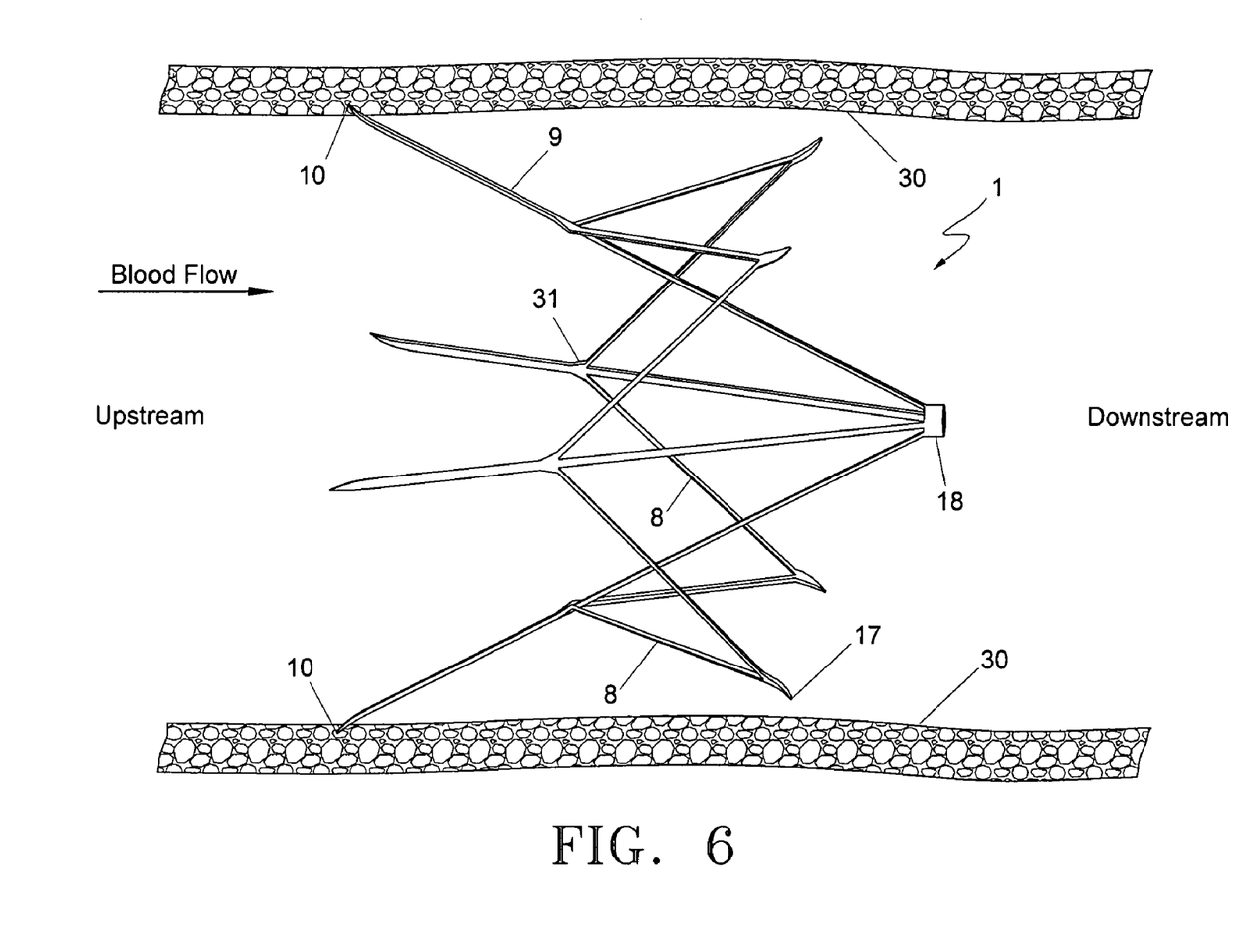
FIG. 6 is a plan view of an alternative embodiment of the vena cava filter device of the present invention.

Other configurations and methods of making a permanent vena cava filter are also possible. For example, FIG. 6 illustrates one alternative configuration of the vena cave filter 1 of the current invention. Although not apparent in FIG. 6 due to the spatial orientation of the device 1, all the barbs at apexes 17 are in contact with the inner wall of vessel 30. In this embodiment, the upstream ends of the zigzag alignment struts 8 are joined to the filter struts 9 at a location 31, which is downstream from the end 10 and upstream from the hub 18. The downstream ends 17 of the alignment struts 8 in the deployed state extend radially from the point 31 in a downstream direction and away from the longitudinal axis of the filter section 20. This orientation results in minimal point contact with the inner wall of vessel 30. Alignment struts 8, joined at an intermediate zone, preferably a mid-zone point 31 of leg 9, only contact the vessel 30 at the downstream end 17. The intermediate zone may be located anywhere along the length of filter strut 9 away from the hub 18 and apex 10.

This design provides the advantage of minimal wall contact between the device 1 and the inner wall of vessel wall 30, resulting in less neointimal incorporation of the filter into the vessel wall. Neointimal buildup may lead to an overall reduction in the diameter of the vena cava due to thickening of the inner wall as well as creating the potential for filter-induced thrombus. Another advantage of the design illustrated in FIG. 6 is the increased filtering efficiency created by the struts 8, which act to provide a secondary level of clot filtering. The construction of this design also involves less metal mass due to the shortened struts 8, which results in less vessel reaction and the ability to utilize a smaller introducer system during deployment.

The method of filter deployment will now be described. To place the filter 1 percutaneously, a delivery device (comprising an inner tube and an outer tube, not shown) containing the filter 1 in a collapsed undeployed state is advanced under fluoroscopy, usually through the jugular vein, into the vena cava. The delivery device is preferably a coaxial tube system with the inner tube removeably connected to hub 18 of the filter. Once correct positioning within the vena cava has been confirmed, the filter 1 is deployed by retracting the outer tube while maintaining the position of the inner tube. As the outer tube is retracted, the filter is uncovered and expands to its preformed deployed state, as shown in FIG. 5.

Advantageously, the present filter 1 allows the operator to reposition the filter after partial deployment by retracting the filter 1 into the delivery system and then repositioning within the vena cava. Once the device has been repositioned in the desired location, the device can be fully deployed using the method described above. Other deployment methods and delivery systems well known in the art can also be used to place the filter and disconnect the filter device from the delivery system. Thus, the filter device 1 of the present invention is easy to deploy through a small delivery system and can be repositioned within the vessel after partial deployment. Another advantage of the current filter device 1 is that the filter is deployed symmetrically within the vessel. Problems with tilting, leg-crossing and asymmetrical axial alignment of struts are eliminated by the interconnecting strut design. Each strut 8 of the centering section 21, because it is connected at the apex to the adjacent strut, will automatically align symmetrically against the vessel wall, regardless of the individual anatomical profile of the vessel.

A femoral vein approach for deployment may sometimes be preferred. The vena cava filter of the current invention may be deployed from either approach. With the femoral approach, the filter is positioned within a delivery sheath in the opposite longitudinal orientation so that the hub end of the filter is deployed first.

The foregoing specific embodiments represent just some of the ways of practicing the present invention. Many other embodiments are possible within the spirit of the invention. Other modifications to the details illustrated in this disclosure, including filter and component shapes, dimensions, barb configurations, materials, methods of construction and methods of use are possible. Accordingly, the scope of the invention is not limited to the foregoing specification, but instead is given by the appended claims along with their full range of equivalents.

What is claimed is:

1. A blood clot filter having an axis and a deployed state comprising:
    a hub;
    a plurality of filter struts extending in an upstream direction from said hub, said filter struts having radially outward upstream ends in the deployed state;
    a plurality of alignment struts, each having a downstream end and an upstream end;
    each of said downstream ends of said alignment struts forming a downstream junction with a downstream end of an adjacent alignment strut; said downstream junctions being radially displaced from said hub when the filter is in the deployed state,
    each of said upstream ends of said alignment struts forming an upstream junction with an upstream end of an adjacent alignment strut,
    each of said upstream junctions forming a junction with one of said filter struts, wherein each of said upstream junctions is located at an intermediate zone of said filter struts and is located radially inwardly relative to each of said downstream junctions and said upstream ends of said filter struts to prevent said alignment struts from lying against a vessel wall in the deployed state;
    said filter struts and said alignment struts at least partially overlapping in an axial direction.

2. The blood clot filter of claim 1 wherein: said hub, said filter struts and said alignment struts are formed from a single tubular element.

3. The blood clot filter of claim 1 wherein: the plurality of alignment struts are arranged in a zigzag pattern.

4. The blood clot filter according to claim 1 wherein: said upstream junctions are radially displaced from said hub when the filter is in a deployed state.

5. A blood clot filter having an axis and a deployed state comprising:
    a hub;
    a plurality of filter struts extending upstream from said hub, said filter struts having radially outward upstream ends in the deployed state;
    a plurality of alignment struts, each having a downstream end and an upstream end;
    each of said downstream ends of said alignment struts forming a downstream junction with a downstream end of an adjacent alignment strut, said downstream junctions being radially displaced from said hub when the filter is in a deployed state;
    each of said upstream ends of said alignment struts forming an upstream junction with an upstream end of an adjacent alignment strut and with an upstream end of one of said filter struts;
    said filter struts and said alignment struts at least partially overlapping in an axial direction;
    said hub, said filter struts and said alignment struts together are integral and made from a single tubular element.

6. The blood clot filter of claim 5 wherein: the entire lengths of said alignment struts in the deployed state are positioned to rest against a vessel inner wall.

7. A blood clot filter comprising:
    a conical filter section having a hub and a plurality of filter struts extending upstream and radially outward from the hub; and
    an alignment section having a plurality of alignment struts, each alignment strut having an upstream end that forms an upstream junction with an upstream end of an adjacent alignment strut and with one of said filter struts,
    each alignment strut having a downstream end that forms a downstream junction with a downstream end of an adjacent alignment strut, each of said downstream junctions being radially displaced from the hub,
    at least a substantial portion of said alignment section overlapping with the conical filter section in an axial direction of said conical filter section; and
    said hub, said filter struts and said alignment struts together are integral and made from a single tubular element.

8. The blood clot filter according to claim 7 wherein: each of said upstream junctions is at an upstream end of one of said filter struts.

9. The blood clot filter according to claim 8 wherein: the entire lengths of each of said alignment struts is adapted to rest against a vessel inner wall.

10. The blood clot filter according to claim 7 wherein: each of said upstream junctions are at an intermediate zone of said filter struts to minimize contact with a vessel inner wall.

11. The blood clot filter according to claim 7 wherein:
    said upstream end of each alignment strut forms a junction with said upstream end of an adjacent alignment strut and with an upstream end of one of said filter struts.

* * * * *